US012617600B2

(12) United States Patent
Infanger et al.

(10) Patent No.: US 12,617,600 B2
(45) Date of Patent: May 5, 2026

(54) NEEDLE DISPENSER

(71) Applicant: Verena Solutions LLC, Chicago, IL (US)

(72) Inventors: Michael Infanger, Park Ridge, IL (US); Michael A. Carvajal, Medford, MA (US)

(73) Assignee: Verena Solutions LLC, Chicago, IL (US)

( * ) Notice: Subject to any disclaimer, the term of this patent is extended or adjusted under 35 U.S.C. 154(b) by 1152 days.

(21) Appl. No.: 17/384,163

(22) Filed: Jul. 23, 2021

(65) Prior Publication Data

US 2022/0024676 A1 Jan. 27, 2022

Related U.S. Application Data

(60) Provisional application No. 63/055,675, filed on Jul. 23, 2020.

(51) Int. Cl.
| | |
|---|---|
| *B65D 83/02* | (2006.01) |
| *A61B 17/06* | (2006.01) |
| *A61B 50/30* | (2016.01) |
| *A61M 5/00* | (2006.01) |
| *B65G 43/08* | (2006.01) |
| *B65G 47/14* | (2006.01) |

(52) U.S. Cl.
CPC ........ *B65D 83/02* (2013.01); *A61B 17/06114* (2013.01); *A61B 50/30* (2016.02); *A61M 5/002* (2013.01); *B65G 43/08* (2013.01); *B65G 47/1478* (2013.01); *A61M 2207/10* (2013.01)

(58) Field of Classification Search
CPC ........ A24C 5/325; A61B 50/30; A61M 5/002; A61M 2207/10; B65B 35/08; B65D 83/02; B65G 29/00; B65G 43/08; B65G 47/84; B65G 47/848; B65G 47/1457; G07F 11/44
See application file for complete search history.

(56) References Cited

U.S. PATENT DOCUMENTS

| | | | | |
|---|---|---|---|---|
| 3,301,396 A | * | 1/1967 | Benson | ................. B07C 5/3412 |
| | | | | 209/530 |
| 3,605,744 A | | 9/1971 | Dwyer | |
| 3,709,328 A | * | 1/1973 | Mohr | ...................... B07C 5/365 |
| | | | | 209/907 |

(Continued)

FOREIGN PATENT DOCUMENTS

CN 204008493 U * 12/2014

*Primary Examiner* — Gene O Crawford
*Assistant Examiner* — Kelvin L Randall, Jr.
(74) *Attorney, Agent, or Firm* — Andrus Intellectual Property Law, LLP

(57) ABSTRACT

A needle dispenser includes a hopper configured to receive and hold a plurality of bulk needles for dispensing. A singularizing drum is positioned to rotate with a portion of the singularizing drum exposed to the interior of the hopper. The singularizing drum includes at least one groove in an outer surface of the singularizing drum. A positioning drum positioned to rotate adjacent to the singularizing drum. The positioning drum includes at least one groove in an outer surface of the positioning drum. The singularizing drum and the positioning drum rotate in coordination to pass a needle from the at least one groove of the singularizing drum to the at least one groove of the positioning drum.

13 Claims, 9 Drawing Sheets

(56)                References Cited

U.S. PATENT DOCUMENTS

| | | | | |
|---|---|---|---|---|
| 3,715,056 | A * | 2/1973 | Preston | A24C 5/3418 |
| | | | | 198/455 |
| 3,820,652 | A | 6/1974 | Thackston | |
| 3,933,239 | A * | 1/1976 | Yoshida | A61J 3/074 |
| | | | | 198/384 |
| 4,063,633 | A * | 12/1977 | Hall | A24C 5/325 |
| | | | | 198/455 |
| 4,266,477 | A * | 5/1981 | Ackley | B41F 17/36 |
| | | | | 198/380 |
| 4,295,558 | A * | 10/1981 | Heckmann | B65G 47/846 |
| | | | | 209/523 |
| 4,331,434 | A * | 5/1982 | Buschor | B31F 1/0054 |
| | | | | 493/135 |
| 4,434,818 | A * | 3/1984 | Yeh | B21F 45/22 |
| | | | | 72/191 |
| 4,648,235 | A * | 3/1987 | Oberdorf | B65B 19/28 |
| | | | | 53/151 |
| 4,741,428 | A * | 5/1988 | Taniguchi | B65G 47/1485 |
| | | | | 198/453 |
| 5,222,502 | A | 6/1993 | Kurose | |
| 5,232,100 | A * | 8/1993 | Lewis | A24C 5/343 |
| | | | | 73/49.8 |
| 5,322,185 | A * | 6/1994 | Leight | A61F 11/08 |
| | | | | 221/265 |
| 6,485,469 | B1 | 11/2002 | Stewart et al. | |
| 7,059,105 | B2 * | 6/2006 | Tabuchi | B29C 65/18 |
| | | | | 53/553 |
| 7,674,218 | B2 * | 3/2010 | Evans | A24D 3/0254 |
| | | | | 83/161 |
| 7,930,066 | B2 * | 4/2011 | Eliuk | A61J 3/002 |
| | | | | 221/9 |
| 10,045,558 | B2 * | 8/2018 | Henley | A24D 3/0287 |
| 10,342,930 | B1 | 7/2019 | Infanger et al. | |
| 10,787,355 | B2 * | 9/2020 | Kuwano | B67C 7/0053 |
| 10,889,453 | B2 * | 1/2021 | Bertoldo | A24D 3/0216 |
| 2003/0205147 | A1 * | 11/2003 | Schackmuth | A47J 37/1228 |
| | | | | 99/336 |
| 2006/0052899 | A1 * | 3/2006 | Shendege | B65B 61/22 |
| | | | | 700/220 |
| 2009/0266126 | A1 * | 10/2009 | Saville | B21D 51/2692 |
| | | | | 72/18.2 |
| 2011/0078980 | A1 * | 4/2011 | Pipes | B65B 35/52 |
| | | | | 53/234 |
| 2011/0124028 | A1 * | 5/2011 | Robinson | G01N 35/00603 |
| | | | | 248/346.03 |
| 2016/0038377 | A1 * | 2/2016 | Tegborg | A61J 7/02 |
| | | | | 221/10 |
| 2016/0159554 | A1 * | 6/2016 | Daniels | B65G 47/1492 |
| | | | | 221/253 |
| 2017/0129079 | A1 * | 5/2017 | Ota | B25B 23/045 |
| 2018/0297791 | A1 * | 10/2018 | Wilson | C12M 41/36 |

* cited by examiner

NEEDLE DISPENSER

CROSS-REFERENCE TO RELATED APPLICATIONS

The present application claims priority to U.S. Provisional Patent Application No. 63/055,675, filed on Jul. 23, 2020, the contents of which is incorporated by reference herein in its entirety.

BACKGROUND

Needles and syringes are frequently used in the delivery of medical care. Needles or syringes may be used to collect samples, for example in the drawing of a blood sample. Needles or syringes may further be used to administer curative or palliative substances, including but not limited to, the administration of anesthesia. Needles or syringes are frequently manufactured in full or in part to be single-use devices. Single-use of needles and/or syringes or portions thereof are known to reduce transmission of disease and help to prevent contamination of the substance being administered or collected. Non-limiting examples of needles and syringes are found in U.S. Pat. Nos. 3,605,744; 3,820,652; 5,222,502; 6,485,469; and 10,342,930, all of which are incorporated by reference herein in their entireties.

Syringes used to administer local anesthetics use a disposable cartridge of local anesthetic and a disposable needle, which attaches to and forms the end of the syringe. The disposable needle is supplied by the manufacturer with a two-part protective cover. The back part of the cover fits over the mounting hub of the needle and extends one centimeter past a back end of the front cover and is removed when the syringe is loaded for use. The front portion remains as a protective cover to preserve the sterility of the needle and to protect a user while handling the syringe prior to and after use. The front portion of the protective cover is referred to as a "needle cap." An annular ridge or shoulder is created spaced apart from the back end of the front portion of the cap, due to the manner in which the back portion of the cover telescopes over the front portion and the two are sealed together. All commercially available needles for dental office use at this time have a similar ridge or shoulder as the apparatus used to attach the needle to most dental syringes is the same. The needles and their protective needle caps intended for use in dental offices are supplied in different lengths for use in Mandibular and Maxillary injections. The Mandibular needle cap is often 4.5 to 5 centimeters long from the previously mentioned shoulder to the front end and the Maxillary needle cap is often 3 to 3.5 centimeters long between those points. The diameter of the cap at the shoulder is typically 1 centimeter and immediately behind the shoulder the diameter is less, usually 0.85 centimeters.

However, manufacturing needles and syringes with these tolerances present challenges as well. Needles may, for example, range from 25 gauge (e.g. 0.51 mm od) to 30 gauge (e.g. 0.31 mm od) and may exemplarily range between 20 and 70 mm in length. It will be recognized that these ranges are merely exemplary and that other needle lengths and diameters may be used or considered within the scope of the present disclosure. Manufacturing the disposable needles, for example in combination with a hub, cap, and/or syringe, requires individualizing the needles and precisely locating this component relative to the hub.

BRIEF DISCLOSURE

An example of a needle dispenser includes a hopper configured to receive and hold a plurality of bulk needles for dispensing. A singularizing drum is positioned to rotate with a portion of the singularizing drum exposed to the interior of the hopper. The singularizing drum includes at least one groove in an outer surface of the singularizing drum. A positioning drum is positioned to rotate adjacent to the singularizing drum. The positioning drum includes at least one groove in an outer surface of the positioning drum. The singularizing drum and the positioning drum rotate in coordination to pass a needle from the at least one groove of the singularizing drum to the at least one groove of the positioning drum.

In further examples of the needle dispenser the positioning drum includes a center shaft and two exterior flanges extend radially away from the center shaft and the at least one groove extends across both of the two exterior flanges. The diameter of the singularizing drum is equal to a diameter of the two exterior flanges of the positioning drum. The positioning drum includes at least one magnet embedded within the positioning drum adjacent the at least one groove. The at least one magnet facilitates transfer of the needle from the singularizing drum to the positioning drum. A scraper may be positioned relative to the singularizing drum. The scraper defines a space between a bottom of the at least one groove of the singularizing drum and the scraper to permit a single needle to pass therethrough.

The singularizing drum includes at least four grooves and the positioning drum includes at least four grooves, wherein the singularizing drum has a rotation increment for each of the at least four grooves in the singularizing drum and the positioning drum has a rotation increment for each of the at least four grooves in the positioning drum. The singularizing drum and the positioning drum incrementally rotate in coordination through successive rotation increments of the singularizing drum and the positioning drum.

A needle sensor is arranged relative to the positioning drum. The needle sensor produces a sensor signal indicative of the presence of a needle relative to the needle sensor. The needle sensor may be a Hall Effect sensor. A controller may receive the sensor signal indicative of the presence of the needle and upon detecting the presence of the needle, the controller operates the positioning drum to rotate one rotation increment to position the needle at a dispense position. The controller operates the positioning drum to maintain the dispense position until the controller receives a signal indicative that the needle has been removed from the positioning drum. A position sensor is configured to sense a rotational position of the positioning drum, wherein the position sensor provides a sensor signal indicative of a rotation increment of the positioning drum. The controller operates to rotate the singularizing drum and the positioning drum through successive rotation increments until the controller receives the sensor signal indicative of the present of the needle. The singularizing drum and the positioning drum are operated to rotate in coordination such that the at least one groove the singularizing drum and the at least one groove of the positioning drum align at a transition point between the singularizing drum and the positioning drum. The at least one groove of the singularizing drum is four grooves evenly spaced about the circumference of the singularizing drum and the at least one groove of the positioning drum is four grooves evenly spaced about the circumference of the positioning drum.

An example of a needle dispensing system includes a hopper configured to receive and hold a plurality of bulk needles for dispensing. A singularizing drum positioned to rotate with a portion of the singularizing drum exposed to the interior of the hopper, the singularizing drum includes at least one groove in an outer surface of the singularizing drum. A positioning drum includes a center shaft and two exterior flanges that extend radially away from the center shaft positioned to rotate adjacent to the singularizing drum. The positioning drum includes a plurality of grooves that extend across the exterior surfaces of both of the two exterior flanges. A plurality of magnets are embedded within the exterior flanges of the positioning drum. Each magnet of the plurality of magnets is embedded radially interior of an exterior surface of the exterior flange and radially interior of a groove of the plurality of grooves. The singularizing drum and the positioning drum rotate in coordination to pass a needle from the at least one groove of the singularizing drum to the at least one groove of the positioning drum.

Further examples of the needle dispensing system include a diameter of the singularizing drum is equal to a diameter of the two exterior flanges of the positioning drum. The singularizing drum has a rotation increment for each groove of the plurality of grooves in the singularizing drum and the positioning drum has a rotation increment for each groove of the plurality of grooves in the positioning drum and the singularizing drum and the positioning drum incrementally rotate in coordination through successive rotation increments of the singularizing drum and the positioning drum. A needle sensor is arranged relative to the positioning drum. The needle sensor produces a sensor signal indicative of the presence of a needle relative to the needle sensor. A controller operates to rotate the singularizing drum and the positioning drum through successive rotation increments until the controller receives the sensor signal indicative of the presence of the needle and upon detecting the presence of the needle. The controller operates, the positioning drum to rotate one rotation increment to position the needle at a dispense position.

An example of a method of dispensing needles includes engaging a plurality of needles against a singularizing drum having a plurality of grooves extending radially interior from an exterior surface of the singularizing drum. The singularizing drum and a positioning drum in coordination. A needle is passed from a groove of the plurality of grooves in the singularizing drum to a groove in the positioning drum. A signal from a needle sensor positioned relative to the positioning drum is analyzed while the singularizing drum and the positioning drum are rotated in coordination. Upon detecting a needle in the signal from the needle sensor, the singularizing drum and the positioning drum are rotated in coordination for a rotation increment. The needle is removed from the positioning drum with a gripping end effector.

DETAILED DISCLOSURE

Figure 1:
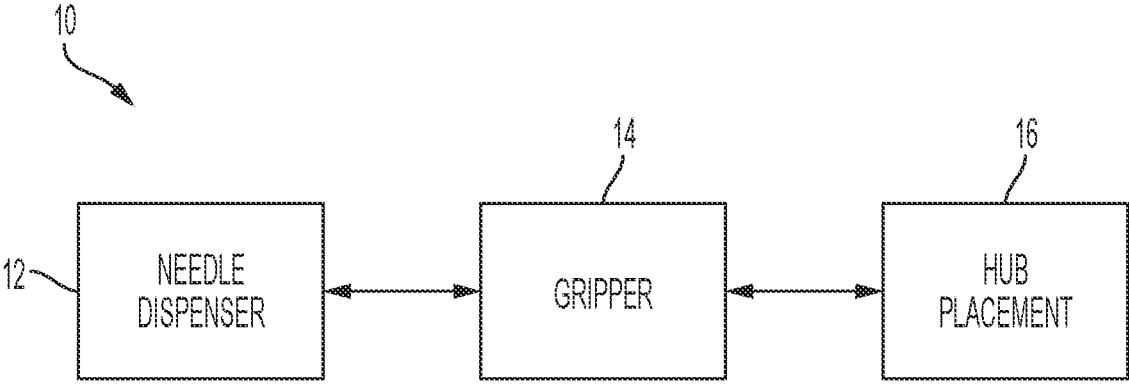
FIG. 1 is a system diagram for the assembly of a needle and a hub.

FIG. 1 presents a system 10 for the assembly of a needle and a hub, for example as used with medical/dental/veterinary needles and syringes. The system 10 includes a needle dispenser 12 which will be described in further detail herein. The needle dispenser 12 receives loose needles in bulk, singularizes the needles and positions a singularized needle for transfer to a gripper 14. The gripper 14 is exemplarily an electro-mechanical arm that engages the needle at the needle dispenser 12 and transfers the needle from the needle dispenser 12 to a hub placement system 16 in which the needle and the hub are positioned in engagement with one another and thus secured. In the example, the combined needle and hub may thus form a completed product and exemplarily the hub may include a Luer lock style connector. In other examples, the combined needle and hub may be fitted to a protective cap. Such combination of a needle, hub and protective cap may itself be an end product of manufacture or may further be connected to a barrel and a plunger to form a syringe.

Figure 2:
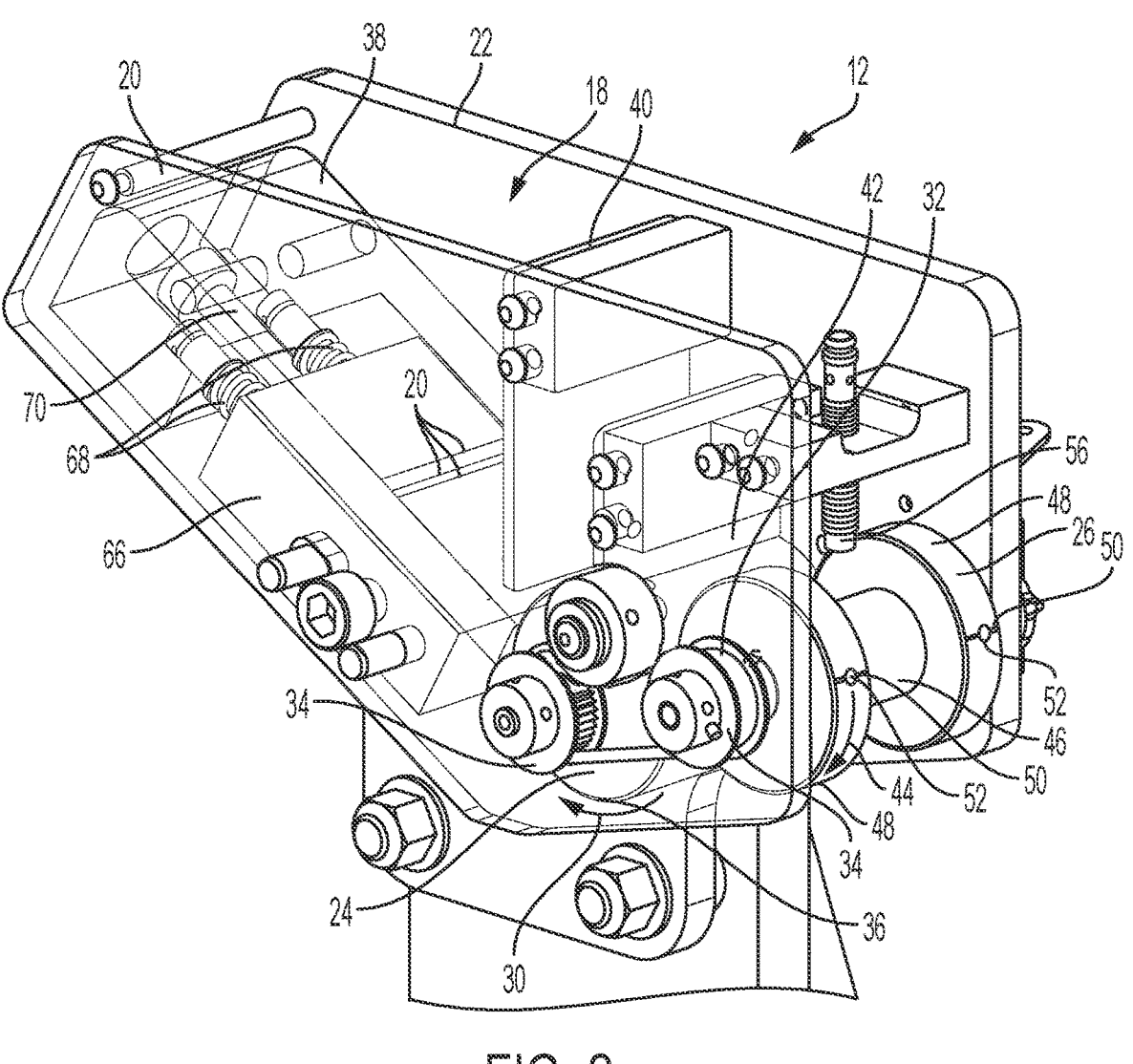
FIGS. 2-4 depict an example of a needle dispenser.
Figure 3:
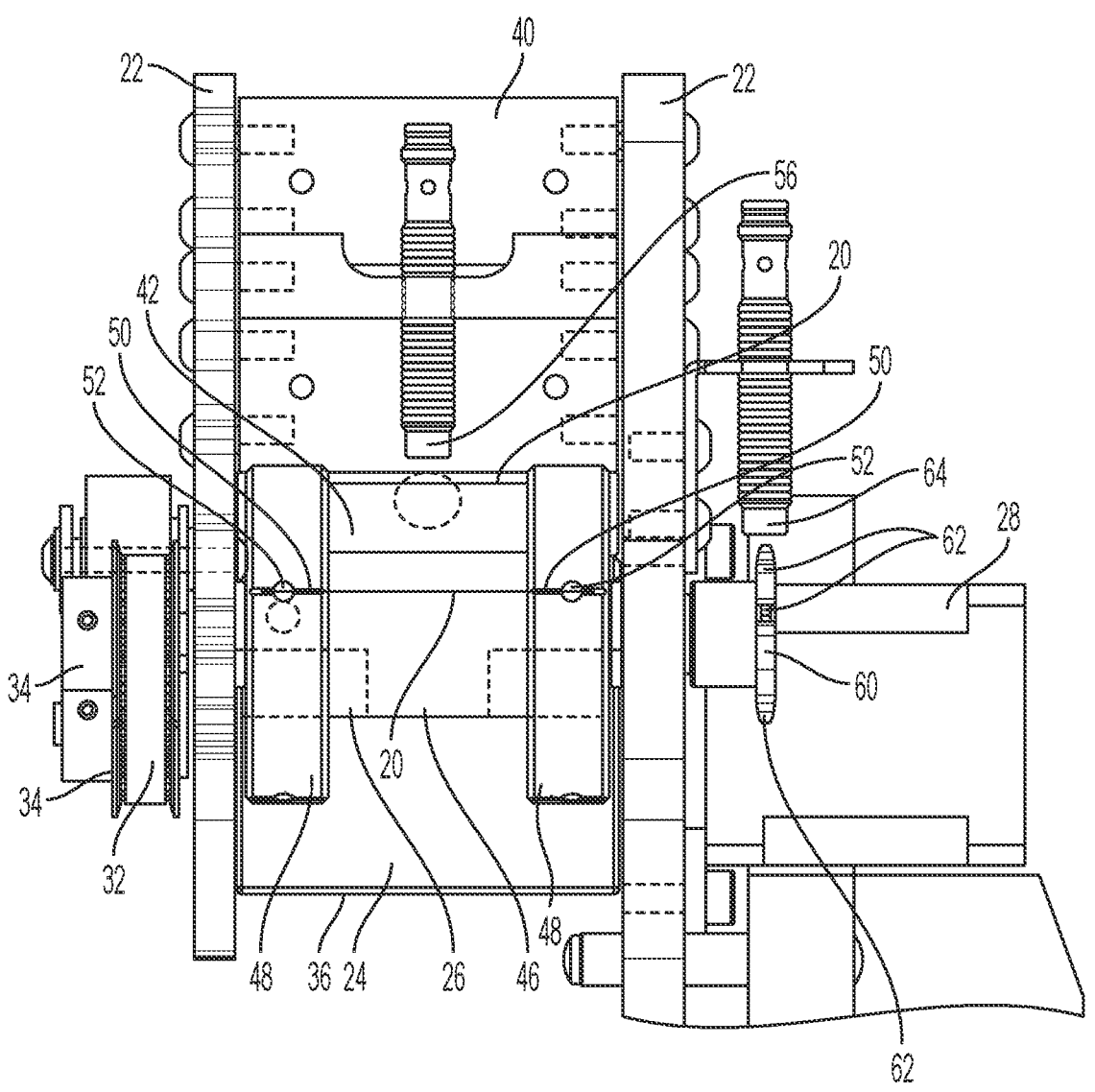
Figure 4:
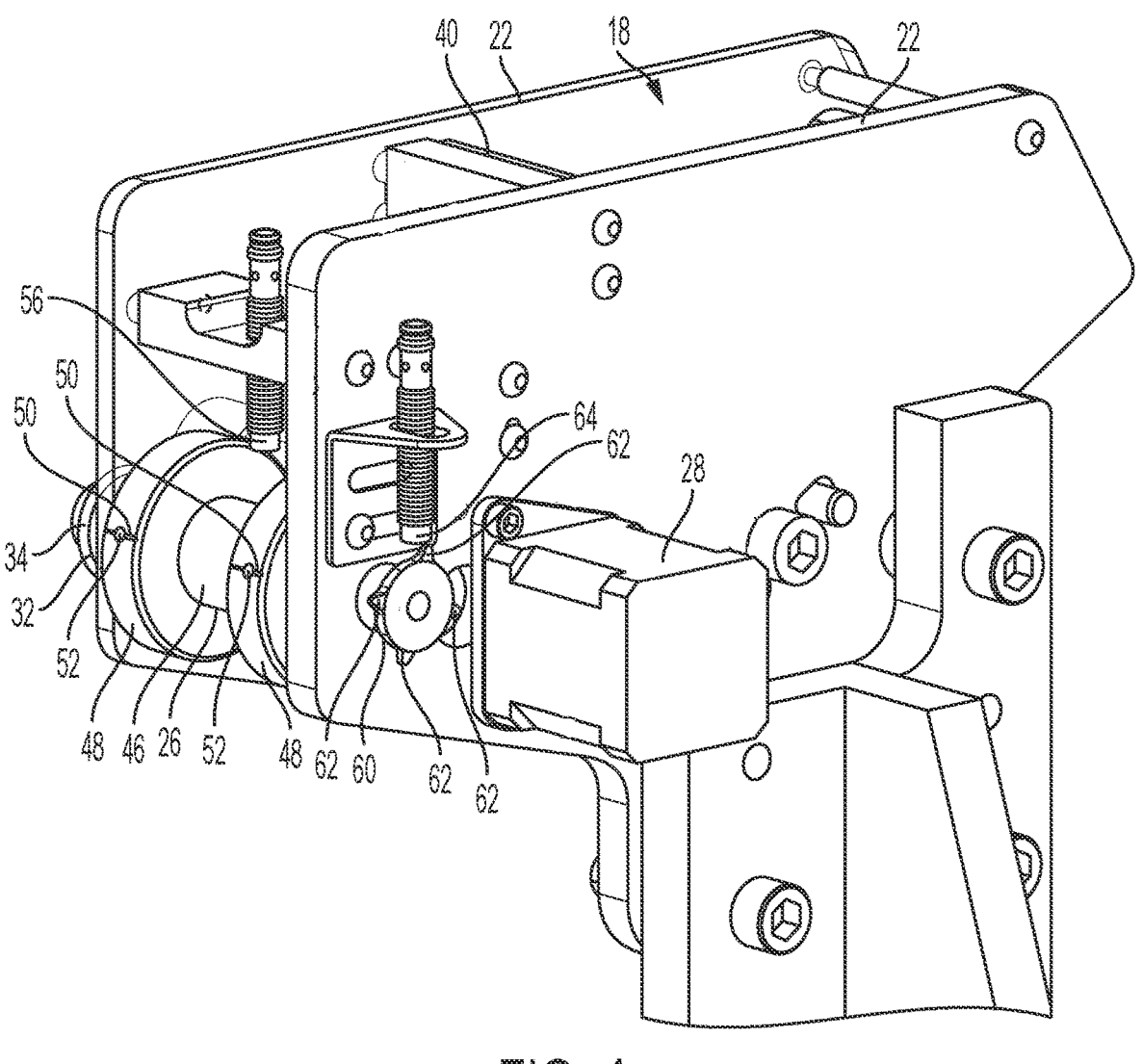

FIGS. 2-4 depict an example of a needle dispenser 12 which will be described in further detail herein.

The needle dispenser 12 includes a hopper 18 that is configured to receive a plurality of loose needles therein. By loose needles, it is recognized that such needles may be provided to the hopper 18 in a package or packaging, for example, a paper wrapping or band around a predefined lot of needles, for example, 100, 200, or 500 needles, although such numeric examples are merely exemplary and it will be recognized that any bulk number of needles may be provided into the hopper 18 of the needle dispenser 12. As shown in FIG. 2, exemplarily, the needles 20 are held within the hopper 18 in an orientation that is generally perpendicular to the length of the hopper 18 and the length overall of the needle dispenser 12. That is, that the needles 20 are generally oriented in a width dimension of the needle dispenser 12 and perpendicular to the direction of movement of the needles through the needle dispenser 12. It will be recognized that the needles 20 may translate within such width dimension within a dimensional tolerance between respective walls 22 that define the hopper 18. It will be recognized that in embodiments, agitation of the hopper 18 and/or tilting of the hopper 18 and/or needle dispenser 12 may assist in aligning the needles 20 in parallel to one another within the hopper 18. Angulation or tilting of the hopper 18 and/or entire needle dispenser 12 may, by gravity, force the needles into slight contact with one of the walls 22 to limit translational error in the position of the needles 20.

The needle dispenser 12 includes two rotating drums. A singularizing drum 24 rotates with a portion of the singularizing drum 24 exposed to the interior of the hopper 18 to pull a single needle from the hopper 18. As described herein, the singularized needle is passed from the singularizing drum 24 to the positioning drum 26 which operates to place the needle in a precise location for transfer to the gripper 14 as previously described. The singularizing drum 24 and the positioning drum 26 are rotated as described in further detail herein. As best depicted in FIG. 5, a motor 28 is operatively connected to the singularizing drum 24 to drive the drum to rotate in the direction of the arrow 30 on FIG. 2. The singularizing drum 24 is operatively connected to the positioning drum 26 by a belt 32. The belt 32 transfers the rotative movement of the singularizing drum 24 from the motor 28 to the positioning drum 26. It will be recognized that the singularizing drum 24 and the positioning drum 26 are configured to have the same outer diameter and therefore when driven by the motor 28 and the rotative power transferred from the singularizing drum 24 to the positioning drum 26 via a belt 32 extending between gear 34 of the same size operate to rotate the singularizing drum 24 and the positioning drum 26 with in-phase rotation. This will be discussed in further detail later herein.

As previously noted, the singularizing drum 24 rotates with a portion of the singularizing drum 24 exposed to the interior of the hopper 18 in which the needles 20 are held. The singularizing drum 24 includes at least one groove 36. Described in further detail herein, the singularizing drum 24 may include four grooves 36 each groove spaced 90 degrees about the circumference of the singularizing drum 24. The at least one groove 36 is dimensioned so as to receive a needle 20 from the hopper 18 therein. Exemplarily, each groove 36 has a width that is slightly larger than the nominal diameter of the needles to be singularized.

The hopper 18 is defined, between the walls 22, in part by an angled hopper floor 38. While examples of the hopper floor 38 will be provided later herein in further detail, generally, the hopper floor 38 is positioned in sliding contact or near contact with the rotating singularizing drum 24 such that the lowermost needles 20 in the hopper 18 are positioned between the hopper floor 38 and a portion of the singularizing drum 24 without any needles being able to fall between the hopper floor 38 and the singularizing drum 24. The singularizing drum 24 may be exemplarily constructed from Dekin® acetal-homopolymer (polyoxymethylene POM) available from DuPont. It will be recognized that other polymer materials, with low friction, low static, and high wear resistance may also be used. A front wall 40 further defines the forward most position of the hopper 18 and in an embodiment is spaced slightly further apart from the singularizing drum 24 than the hopper floor 38 which permits a needle 20 positioned within the groove 36 to rotate with the singularizing drum 24 past the front wall 40 and out of the hopper 18 in the direction of arrow 30. A scraper 42 is positioned exemplarily radially closer to the singularizing drum 24 than the front wall 40 and the scraper 42 ensures that the needle 20 is positioned within the groove 36 and only a single needle within the groove 36 passes beyond the scraper 42. In an example, the scraper 42 is positioned top dead center of the singularizing drum 24.

It will be recognized that in further examples, the scraper may be an optional component or may be arranged in a location or orientation differently than that depicted in, for example, FIG. 2. In one example, the scraper 42 may be located in a different location, while still positioned relative to the singularizing drum 24, while in other examples as described in further detail herein, no scraper 42 is included.

As previously noted, the positioning drum 26 rotates in synchrony with the singularizing drum 24 exemplarily in the direction of arrow 44. The positioning drum 26 is exemplarily constructed from A2 steel and is spool-shaped with a central spindle 46 and exterior cylindrical flanges 48. The cylindrical flanges 48 each have a diameter equal to the diameter of the singularizing drum 24. The central spindle 46 has a smaller diameter than the cylindrical flanges 48. The cylindrical flanges 48 also include grooves 50 to receive a needle 20 therein. The grooves 50 in each of the cylindrical flanges 48 are aligned such that a single needle can be held within both aligned grooves 50 of the cylindrical flanges 48 simultaneously. As with the singularizing drum 24, the positioning drum 26 includes at least one pair of grooves 50, and in the example provided herein, includes four pairs of grooves, each positioned 90 degrees about the circumference of the positioning drum 26. It will be recognized that more or fewer groove pairs may be used but that the groove pairs 50 are consistent in number and spacing with the grooves 36 of the singularizing drum 24. Furthermore, the magnets 52 are embedded within the cylindrical flange 48 at the position of the grooves 50. As depicted in FIGS. 2-4, the magnets 52 may be circular in shape and positioned centrally to the grooves 50. That is, the magnets 52 may be positioned into the cylindrical flange 48 radially interior of the grooves 50

Figure 5A:
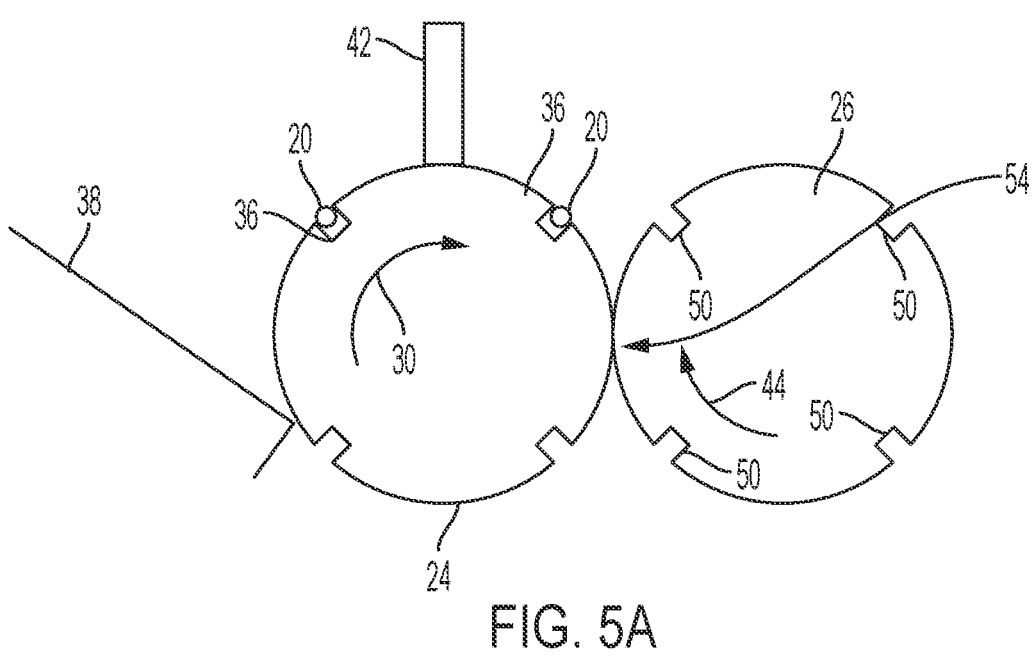
FIGS. 5A-5D depict relative orientations of the singularizing drum and the positioning drum during operation of an example of the needle dispenser.
Figure 5B:
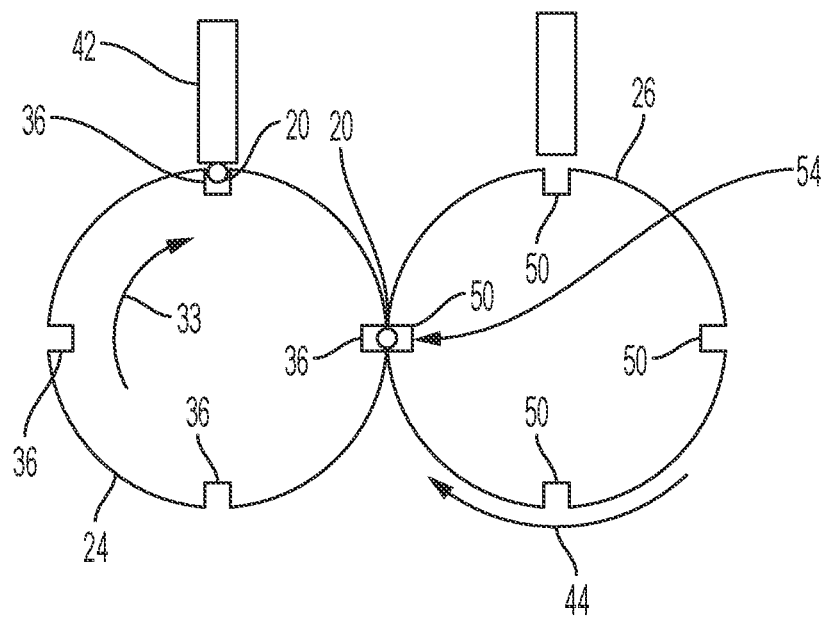

As previously discussed, the singularizing drum 24 and the positioning drum 26 are both simultaneously driven in the directions of arrows 30 and 44. Therefore, as the singularizing drum 24 is rotating forward with a needle 20 positioned within a groove 36, the positioning drum is rotating upwards in the direction of arrow 44 moving a pair of grooves 50 towards a transfer location 54 as depicted in FIG. 5A. In FIG. 5B, the singularizing drum 24 and the positioning drum 26 have rotated approximately an additional 45 degrees and a groove 36 of the singularizing drum 24 containing a needle 20 is in alignment with a groove pair 50 of the positioning drum 26 at the transition location 54. At the transition location 54, the magnets 52 of the positioning drum 26 help to transfer the needle 20 from the groove 36 into the pair of grooves 50. It is further noted that in FIG. 5B the scraper 42 helps to position a subsequent needle 20 within a subsequent groove 36 of the singularizing drum 24. Should the needle 20 be positioned only part-way within the groove 36, or should two needles be drawn upwards by the movement of the singularizing drum 24, the scraper 42 serves to complete the singularization of the needle 20 from the hopper 18.

Figure 5C:
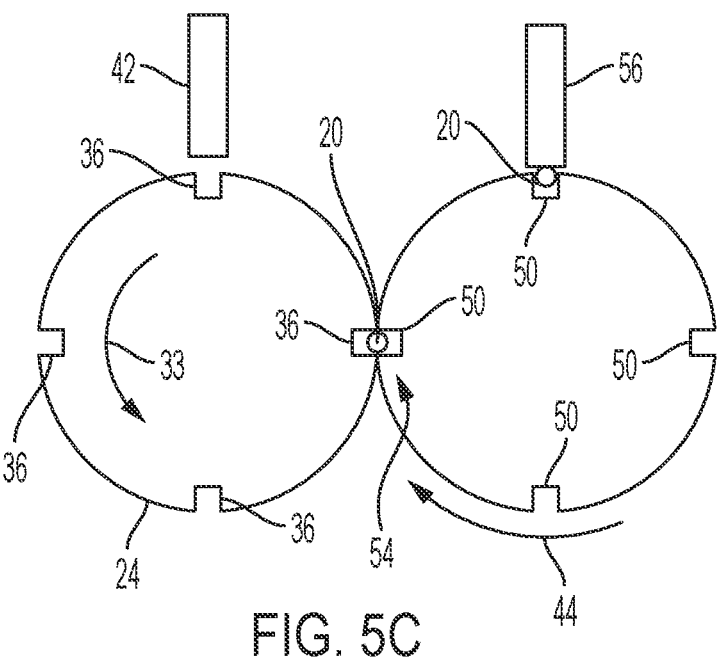
Figure 5D:
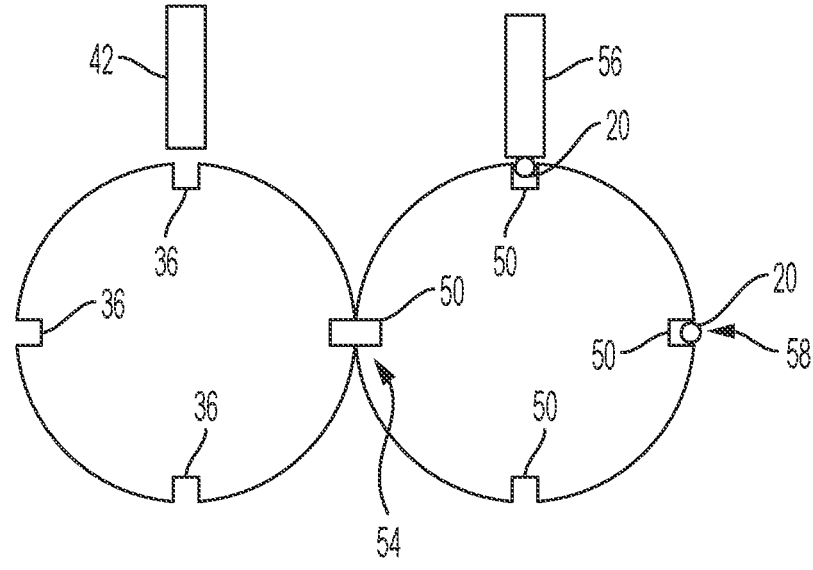

FIG. 5C exemplarily depicts the singularizing drum 24 and the positioning drum 26 after an additional 90 degrees of rotation. The positioning drum 26 has rotated the needle 20 into a position relative to a needle sensor 56. The needle sensor 56 is exemplarily a Hall-effect sensor that determines if a needle 20 is positioned within the pair of grooves 50 positioned near the sensor 56. In additional examples, the sensor 56 may use visible or IR light or another type of position sensor as may be recognized by one of ordinary skill of the art in view of this present disclosure. It is noted that in FIG. 5C, a subsequent needle 20 is located at the aligned grooves 36, 50 at the transition location 54. Thus, this needle 20 is also passed from the groove 36 of the singularizing drum 24 to the pair of grooves 50 of the positioning drum 26. Upon the detection of a needle by the sensor 56 at the position as shown in FIG. 5C, the drums are driven by an additional 90 degrees of rotation to the position as depicted in FIG. 5D. In FIG. 5D, the needle 20 is located at the dispensing location 58 with a needle 20 held at the dispensing location 58, the electromechanical actuator of the gripper 14 can operate to grasp the needle 20. The known and consistently repeatable dispensing location 58 enables efficient and accurate operation of such a gripper to consistently engage the needle 20 with both prompts gripping success as well as consistent gripping position facilitating proper engagement of the needle subsequently with the hub as previously described.

The needle dispenser 12 exemplarily includes a digital computer exemplarily in the form of a programmable logic controller (PLC) that operates to receive input signals from components of the needle dispenser exemplarily as described herein and/or from other components of the assembly system 10 as described herein and to output control signals, exemplarily to the motor 28 to drive the singularizing drum 24 and the positioning drum 26 in the manner described with respect to FIG. 5 in response to such input.

Figure 6:
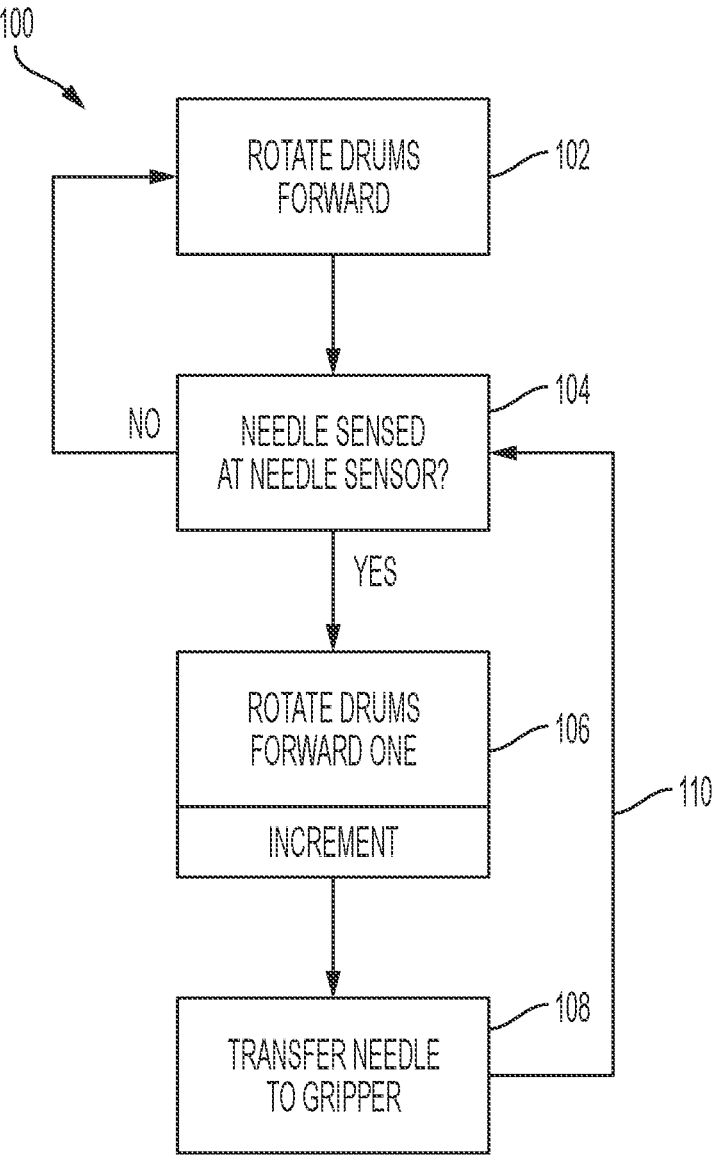
FIG. 6 is a flowchart that depicts an exemplary embodiment of a method of operation of a needle dispenser

FIG. 6 is a flowchart that depicts an exemplary embodiment of a method 100 of operation of the needle dispenser 12 as may be carried out by operations of the PLC. At 102, the motor 28 receives a signal to rotate the drum forward exemplarily in the direction of arrows 30 and 44. The PLC receives signals from the needle sensor 56 to determine if a needle is sensed by the needle sensor 56. If no signal indicating a sensed needle is received, then the PLC continues to have the motor operate to rotate the drums forward. It is to be noted that because the singularizing drum 24 is attempting to pull a single needle from the plurality of needles held in the hopper 18 that as the singularizing drum 24 rotates, some grooves 36 of the singularizing drum will not retain a needle. This may be due to happenstance positioning wherein multiple needles attempt to fall into the groove 36 due to gravity and block each other from entering the groove 36, or a misaligned needle may be knocked out of the groove 36 by the scraper 42. In any event, a needle can only be transferred to the positioning drum 26 and thus be sensed by the needle sensor 56 if it is first pulled from the hopper 18 by the singularizing drum 24. Therefore, the feedback loop at 104, the drums are rotated forward until a needle is sensed at the needle sensor 56, for example as depicted in FIG. 5C.

Referring to FIGS. 3 and 4, the positioning drum 26 includes a positioning sprocket 60. The positioning sprocket includes one or more teeth 62 that correspond in number and position to the pairs of grooves 50 of the positioning drum 26. Thus, each of the teeth 62 of the sprocket 60 represents a rotation increment of both the positioning drum 26 and the singularizing drum 24. A position sensor 64, which may also be a Hall effect sensor or another sensor as previously described or as will be recognized in view of the present disclosure, senses the alignment and/or passing of each of the teeth 62 with the sensor 64. In such example, the sensor 64 provides the PLC (not depicted) with the input feedback to know the rotational position of the positioning drum 26 such that the positioning drum can be rotated forward one increment, for example at 106 of FIG. 6 as will be explained in further detail herein.

Once a needle has been sensed by the needle sensor at 104, the PLC operates to rotate the drums forward one increment at 106. As noted, the grooves 36 in the singularizing drum 24 and the pairs of grooves 50 in the positioning drum 26 are the same in both number and spacing about the respective drum. Thus, the same rotational increments separate each of the grooves. When a needle is sensed at the needle sensor at 104, the drums are rotated to advance the drums to the next increment position. That is, a position in which one of the pairs of grooves 50 is in alignment at the dispensing location 58. In an example, this also aligns a groove 36 of the singularizing drum 24 and a pair of grooves 50 of the positioning drum 26 at the transition location 54. The needle sensor 56 exemplarily detects a needle when in the next increment that needle will be positioned at the dispensing location 58. After rotating the drums forward one increment to position the sensed needle at the dispensing location 58, the drums are held in this position, for example by the PLC providing a control signal to the motor to stop the advancement of the motor 28. The drums are held in this position to facilitate the gripper engaging and removing the needle from the pair of grooves 50 of the positioning drum 26 to continue the manufacturing process of the assembly system 10. A feedback signal 110 from the gripper to the PLC informs the PLC that the gripper has removed the needle from the dispensing location 58 and the PLC operates the motor to rotate the drums forward. Returning to 104, if a needle is located in the immediately subsequent pair of grooves 50 of the positioning drum 26, then the drums are rotated forward one increment at 106 to position this subsequent needle at the dispensing location 58. However, if no needle is in that immediately subsequent pair of grooves 50, then the PLC operates the motor to rotate the drums forward at 102.

Figure 7:
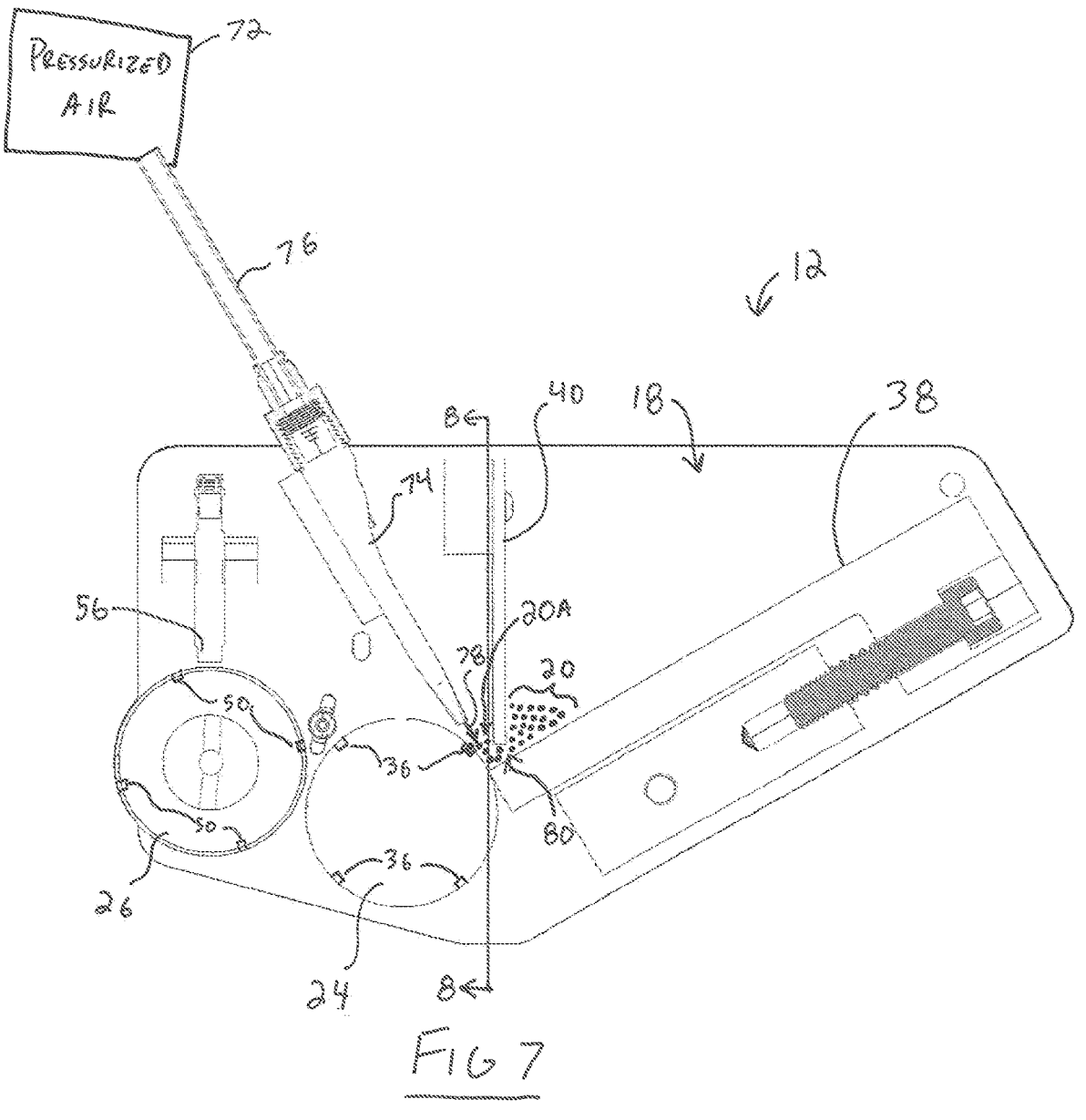
FIG. 7 is a side sectional view of a further example of a needle dispenser.
Figure 8:
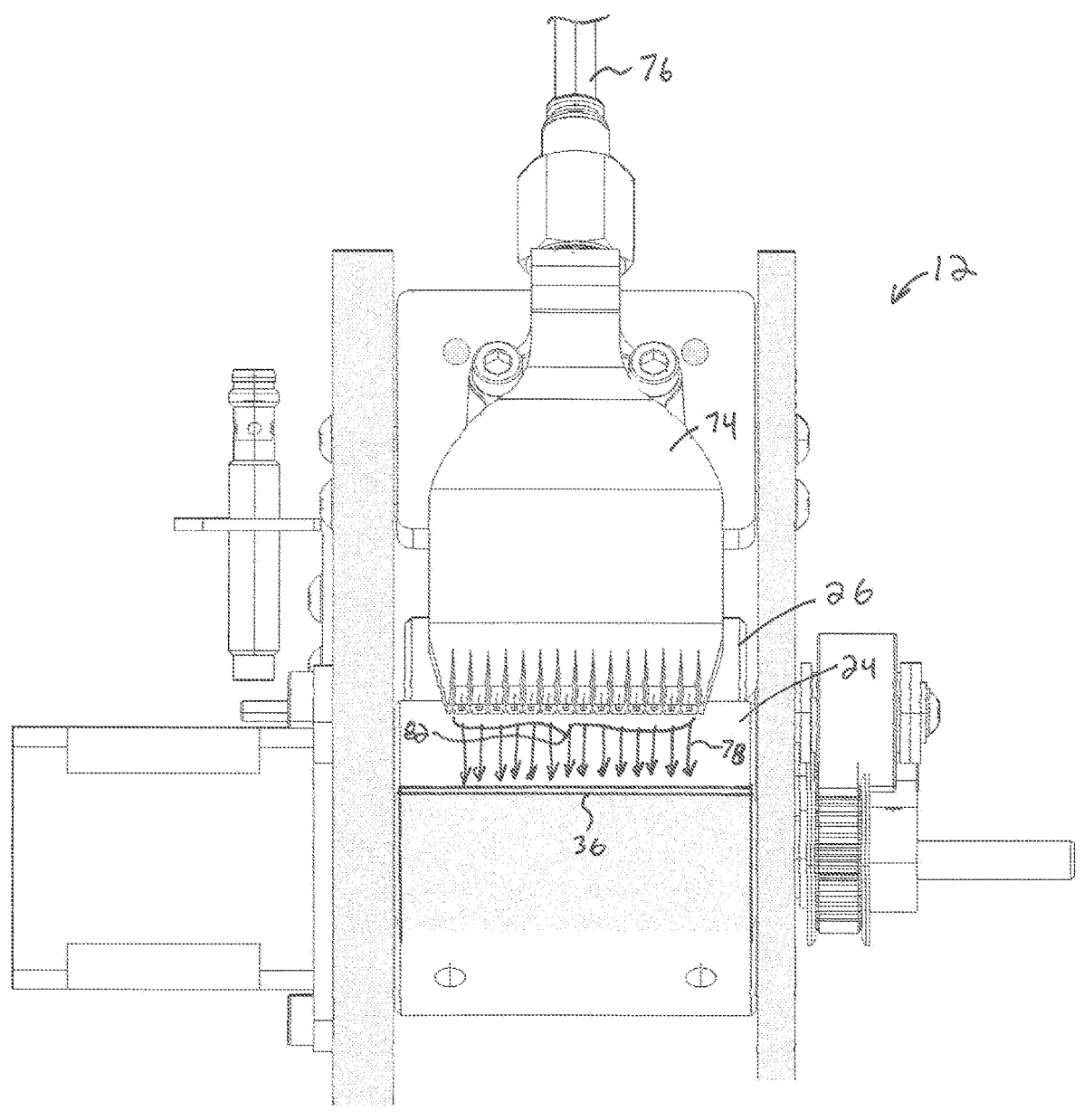
FIG. 8 is a sectional view of the needle dispenser taken along line 8-8 of FIG. 7.

FIGS. 7 and 8 provide sectional views of a further example of the needle dispenser 12. It will be recognized that the features shown in FIGS. 7 and 8 may be combined with any of the other examples or features of the needle dispenser as disclosed herein. In FIGS. 7 and 8, like reference numerals refer to similar components between the examples. As previously noted, examples of the needle dispenser 12 do not include a scraper 42 as previously described. In FIGS. 7 and 8 a source of pressurized air 72 is connected to a plenum 74 by a duct 76. The plenum 74, flattens (see FIG. 7) and widens (see FIG. 8) as the plenum 74 extends away from the duct 76. The plenum is arranged relative to the singularizing drum 24, for example at an angle tangential to the singularizing drum. Additionally or alternatively, the plenum 74 may be arranged perpendicular to the hopper floor 38. The plenum produces an air flow 78 that is tangential or approximately tangential, either contacting the singularizing drum 24 at a small localized area near the hopper floor 38, or the air flow 78 blows past the singularizing drum 24 without contacting the singularizing drum 24 with the primary air flow 78 from the plenum 74.

Instead, the air flow 78 crates an air knife or air curtain within the needle dispenser, wherein if a needle 20 is only partially seated in the groove 36 or two needles 20 are each partially seated in the groove 36, then the air flow 78 catches a portion of one or both of the needles partially seated in the groove and likely blows one or both out of the groove 36 back into the interior accumulation 20A of needles 20 interior of the front wall 40. In other examples, the air flow 78 may help to seat a single needle 20 within the groove. The air flow 78 further helps to limit and constrain an accumulation of needles 20A between the wall 40 and the singularizing drum 24. The wall 40 helps to maintain the bulk of the needles 20 within the hopper 18 behind the wall, while only permitting a smaller number of needles 20 to pass through the gap 80 between the wall 40 and the hopper floor 38. However, needles 20 accumulate between the singularizing drum 24 and the wall 40 and the air flow 78 limits this accumulation while also ensuring that if a needle 20 is in the groove 36, there is only a single needle and that needle is seated within the groove 36. Referring to FIG. 8, the plenum 74 may further taper to a plurality of orifices 82. Each orifice 82 produces an air flow 78 such that the air flow 78 comprises a plurality of component air flows 78.

Referring back to FIG. 2, in a still further example, the hopper floor 38 may include an adjustable floor plate 66. The adjustable floor plate 66 helps to facilitate the positioning of the hopper floor 38 relative to the singularizing drum 24. As previously noted, the hopper floor 38 is positioned sufficiently close to the singularizing drum 24 such that needles 20 cannot fall out of the hopper 18 in a space between the hopper floor 38 and the singularizing drum 24. However, the hopper floor 38 must allow for free movement of the singularizing drum 24 to limit heat and static buildup within the dispenser as well as wear on the singularizing drum 24 and motor 28. The adjustable floor plate 66 is biased by one or more springs 68 into the direction of the singularizing drum 24. Against this biasing, the adjustable floor plate 66 is held into place by a set screw 70. This provides a needle dispensing system that is adjustable to accommodate variation in different needle sizes as well as to accommodate adjustment for wear and use of the singularizing drum.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A needle dispenser comprising:
a hopper defining an interior configured to receive and hold a plurality of bulk needles for dispensing;
a singularizing drum positioned to rotate with a portion of the singularizing drum exposed to the interior of the hopper, the singularizing drum comprising a plurality of grooves at least one groove in an outer surface of the singularizing drum;
a positioning drum positioned to rotate adjacent to the singularizing drum, wherein the positioning drum comprises a center shaft and two exterior flanges that extend radially away from the center shaft and forming an outer surface of the positioning drum, with a plurality of grooves extending across both of the two exterior flanges, the plurality of grooves in the positioning drum matches the plurality of grooves in the singularizing drum, wherein the singularizing drum and the positioning drum each have a rotation increment associated with each of the plurality of grooves in the singularizing drum and the positioning drum, and the singularizing drum and the positioning drum rotate in coordination through successive rotation increments of the singularizing drum and the positioning drum to pass a needle from a groove of the singularizing drum to a groove of the positioning drum and to rotate groove of the positioning drum to a dispense position, wherein the two exterior flanges define a space therebetween configured to accommodate a gripper operable to remove the needle from the dispensing position;
a needle sensor arranged relative to the positioning drum at a rotation increment of the plurality of successive rotation increments immediately prior to the dispense position, wherein the needle sensor produces a sensor signal indicative of a presence of a needle at the rotation increment prior to the dispense position; and
a controller configured to operate the singularizing drum and the positioning drum to rotate through the successive rotation increments until the controller receives the sensor signal indicative of the presence of the needle, and upon detecting the presence of the needle, the controller is configured to operate the positioning drum to rotate one rotation increment to position the needle at the dispense position;
wherein the singularizing drum and the positioning drum are configured to rotate in coordination such that the plurality of grooves in the singularizing drum and the plurality of grooves in the positioning drum align each sequentially align at a transition point between the singularizing drum and the positioning drum.

2. The needle dispenser of claim 1, wherein a diameter of the singularizing drum is equal to a diameter of the two exterior flanges of the positioning drum.

3. The needle dispenser of claim 1, wherein the positioning drum further comprises at least one magnet embedded within the positioning drum adjacent the at least one groove, wherein the at least one magnet facilitates transfer of the needle from the singularizing drum to the positioning drum.

4. The needle dispenser of claim 1, further comprising an air plenum positioned relative to the singularizing drum, wherein air plenum directs a flow of air over a portion of the singularizing drum towards the hopper.

5. The needle dispenser of claim 1, wherein the positioning drum further comprises a plurality of magnets embedded within each exterior flange at positions radially interior of each of the grooves, wherein the plurality of magnets facilitate transfer of the needle from the singularizing drum to the positioning drum.

6. The needle dispenser of claim 1, wherein the needle sensor is a Hall Effect sensor.

7. The needle dispenser of claim 1, wherein the controller operates the positioning drum to maintain the dispense position until the controller receives a signal indicative that the needle has been removed from the positioning drum.

8. The needle dispenser of claim 1, further comprising a position sensor configured to sense a rotational position of the positioning drum, wherein the position sensor provides a sensor signal indicative of a rotation increment of the positioning drum.

9. The needle dispenser of claim 1, wherein the plurality of grooves of the singularizing drum are evenly spaced about a circumference of the singularizing drum and the plurality of grooves of the positioning drum are evenly spaced about a circumference of the positioning drum.

10. A needle dispensing system comprising:
a hopper configured to receive and hold a plurality of bulk needles for dispensing;
a singularizing drum positioned to rotate with a portion of the singularizing drum exposed to an interior of the hopper, the singularizing drum comprising at least one groove in an outer surface of the singularizing drum;

a positioning drum comprising a center shaft and two exterior flanges that extend radially away from the center shaft positioned to rotate adjacent to the singularizing drum, wherein the positioning drum comprises a plurality of grooves that extend across exterior surfaces of both of the two exterior flanges and the two exterior flanges of the positioning drum define a space therebetween configured to accommodate a gripper operable to remove the needle from a dispensing position of the positioning drum; and a plurality of magnets embedded within the exterior flanges of the positioning drum, each magnet of the plurality of magnets embedded radially interior of an exterior surface of the exterior flange and radially interior of a groove of the plurality of grooves;

wherein the singularizing drum and the positioning drum rotate in coordination to pass a needle from the at least one groove of the singularizing drum to the at least one groove of the positioning drum.

11. The needle dispenser of claim 10, wherein a diameter of the singularizing drum is equal to a diameter of the two exterior flanges of the positioning drum.

12. The needle dispenser of claim 11, wherein the singularizing drum has a rotation increment for each groove of the plurality of grooves in the singularizing drum and the positioning drum has a rotation increment for each groove of the plurality of grooves in the positioning drum and the singularizing drum and the positioning drum incrementally rotate in coordination through successive rotation increments of the singularizing drum and the positioning drum.

13. The needle dispenser of claim 12, further comprising:

a needle sensor arranged relative to the positioning drum, wherein the needle sensor produces a sensor signal indicative of the presence of a needle relative to the needle sensor; and a controller that operates to rotate the singularizing drum and the positioning drum through successive rotation increments until the controller receives the sensor signal indicative of the presence of the needle and upon detecting the presence of the needle, the controller operates, the positioning drum to rotate one rotation increment to position the needle at a dispense position.

* * * * *